(12) United States Patent
Weber

(10) Patent No.: US 6,807,440 B2
(45) Date of Patent: Oct. 19, 2004

(54) CERAMIC REINFORCEMENT MEMBERS FOR MRI DEVICES

(75) Inventor: Jan Weber, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 321 days.

(21) Appl. No.: 10/007,284

(22) Filed: Nov. 9, 2001

(65) Prior Publication Data

US 2003/0092984 A1 May 15, 2003

(51) Int. Cl.[7] .............................. A61B 5/05; A61M 25/00
(52) U.S. Cl. ..................... 600/423; 604/524; 604/527
(58) Field of Search .............................. 600/423, 424, 600/523–529; 324/318; 623/1.15

(56) References Cited

U.S. PATENT DOCUMENTS

| | | | | |
|---|---|---|---|---|
| 5,019,090 A | * | 5/1991 | Pinchuk ...................... 623/1.15 |
| 5,728,079 A | | 3/1998 | Weber et al. ................ 604/280 |
| 5,792,401 A | | 8/1998 | Burnham ..................... 264/103 |
| 5,961,511 A | | 10/1999 | Mortier et al. .............. 604/527 |
| 5,962,007 A | * | 10/1999 | Cooper et al. ............... 424/426 |
| 6,017,335 A | | 1/2000 | Burnham ..................... 604/282 |
| 6,024,722 A | * | 2/2000 | Rau et al. ................. 604/96.01 |
| 6,031,375 A | | 2/2000 | Atalar et al. ................ 324/307 |
| 6,171,240 B1 | | 1/2001 | Young et al. ................ 600/410 |
| 6,193,705 B1 | | 2/2001 | Mortier et al. .............. 604/523 |
| 6,475,234 B1 | * | 11/2002 | Richter et al. .............. 623/1.15 |
| 6,508,806 B1 | * | 1/2003 | Hoste ........................ 604/524 |
| 6,520,952 B1 | * | 2/2003 | Jimenez ...................... 604/524 |
| 6,524,345 B1 | * | 2/2003 | Valimaa et al. ........... 623/23.56 |
| 6,628,980 B2 | * | 9/2003 | Atalar et al. ................ 600/423 |

FOREIGN PATENT DOCUMENTS

| | | |
|---|---|---|
| EP | 0 702 976 A | 3/1996 |
| EP | 1 136 085 A | 9/2001 |
| NL | 1 005 946 C | 11/1998 |
| WO | WO 01 49335 A | 7/2001 |

OTHER PUBLICATIONS

Ceramic Composites CMC Oxide—oxide Fiber Manufacture and research. Coi Ceramics located at http://www.coiceramics.com.

Ceramic Fiber Protection Products from 3m.com Ceramic Textile and Composite. Located at www.3m.com/market/industrial/ceramics/index.jhtml.

* cited by examiner

*Primary Examiner*—Shawna J. Shaw
(74) *Attorney, Agent, or Firm*—Westman, Champlin, & Kelly, P.C.

(57) ABSTRACT

The present invention relates to a reinforced magnetic resonance imaging catheter. The catheter comprises an elongated body having at least one lumen extending therethrough. The elongated body also includes a proximal end, a distal end, and circumference, a longitudinal axis running between the proximal and distal ends, and a coaxial layer that incorporates at least one elongated ceramic member. An antenna is operably disposed proximate the distal end the elongated body.

27 Claims, 3 Drawing Sheets

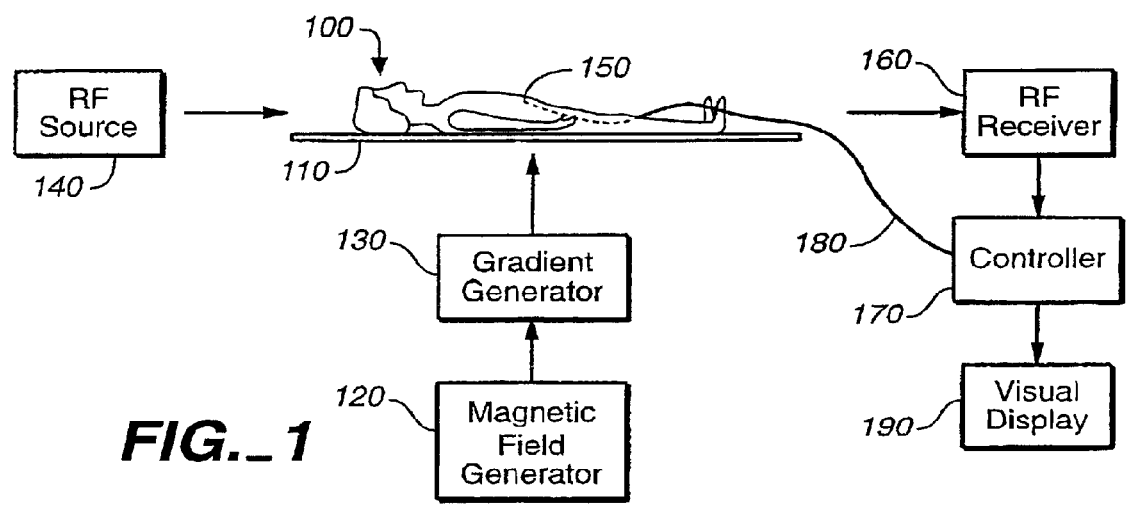
FIG._1

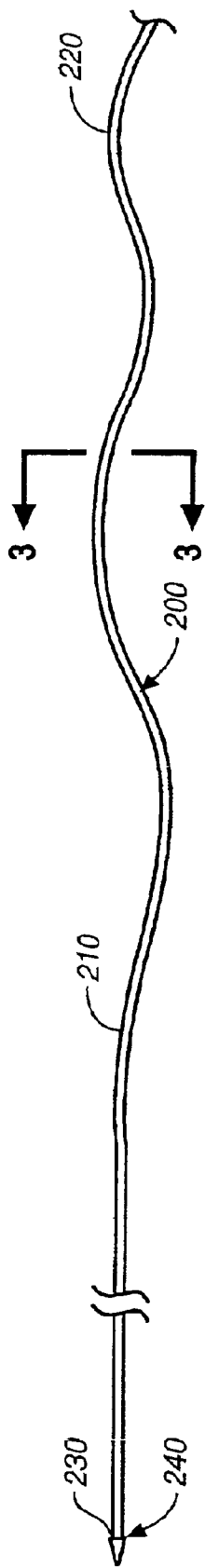
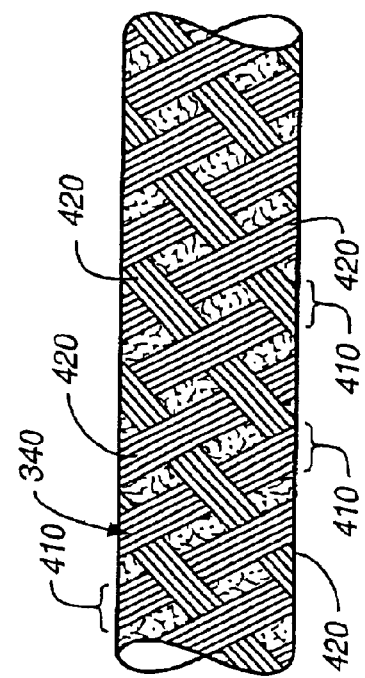
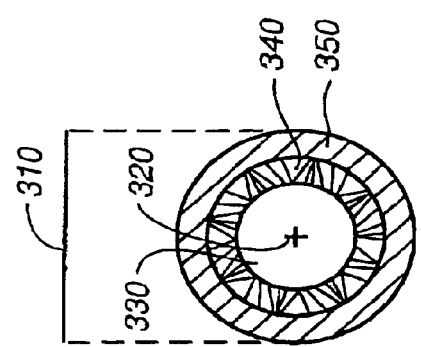

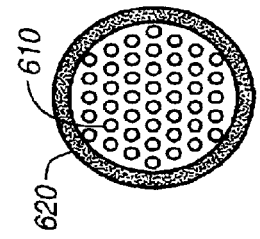
FIG._6
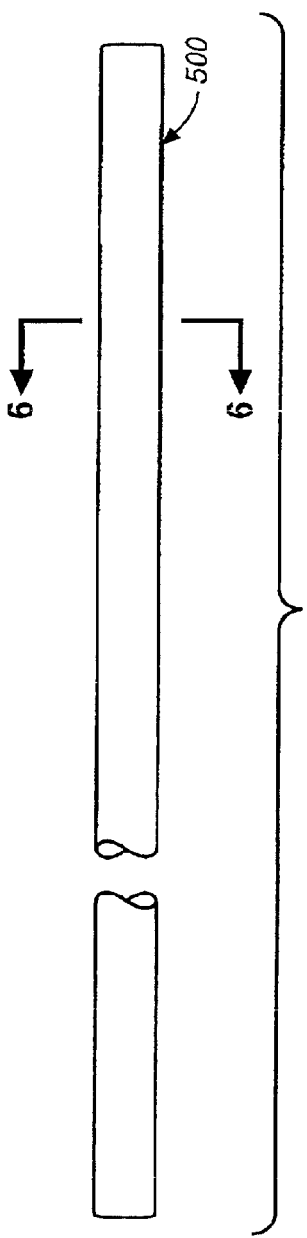
FIG._5
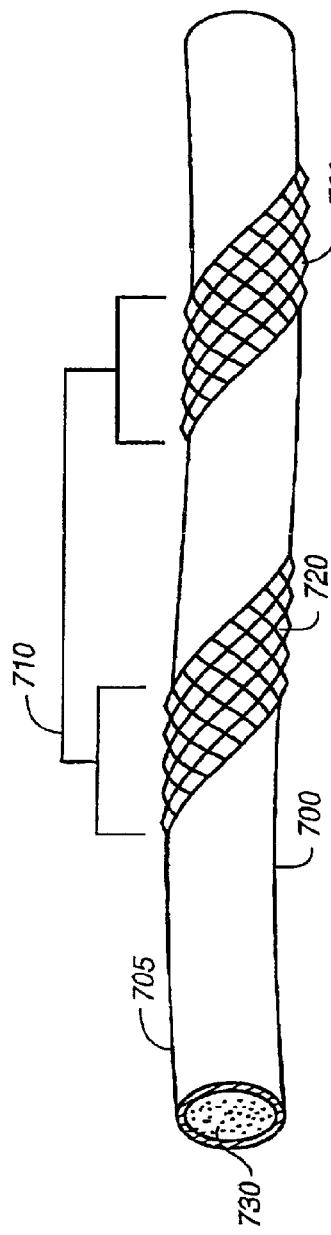
FIG._7
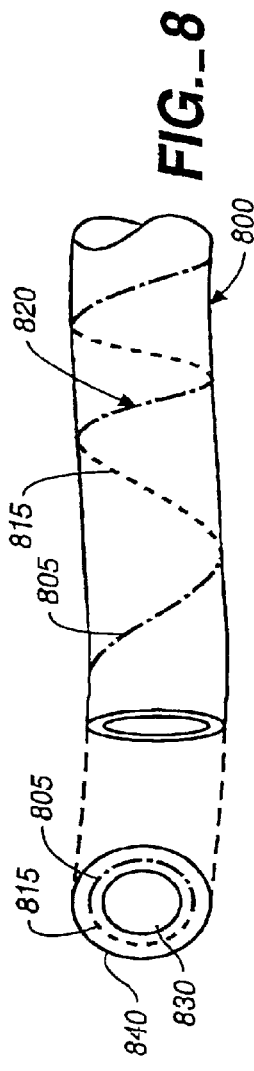
FIG._8

CERAMIC REINFORCEMENT MEMBERS FOR MRI DEVICES

BACKGROUND OF THE INVENTION

The present invention relates generally to intravascular devices used in magnetic resonance imaging. More particularly, the present invention relates to a ceramic reinforcement member for reinforcing elongated intravascular magnetic resonance imaging devices.

Tracking of catheters and other devices positioned within a body may be achieved by means of a magnetic resonance imaging (MRI) system. Typically, such a magnetic resonance imaging system may be comprised of a magnet, a pulsed magnetic field gradient generator, a transmitter for electromagnetic waves in radio frequency (RF), a radio frequency receiver, and a controller. In a common implementation, an antenna is disposed either on the device to be tracked or on a guidewire or a catheter (commonly referred to as a magnetic resonance catheter or an MR catheter) used to assist in the delivery of the device to its destination. In one known implementation, the antenna comprises an electrically conductive coil that is coupled to a pair of elongated electrical conductors that are electrically insulated from each other, and that together comprise a transmission line adapted to transmit the detected signal to the RF receiver.

In one embodiment, the coil is arranged in a solenoid configuration. A patient is placed into or proximate the magnet and the device is inserted into the patient. The magnetic resonance imaging system generates electromagnetic waves in radio frequency and magnetic field gradient pulses that are transmitted into the patient and that induce a resonant response signal from selected nuclear spins within the patient. This response signal induces current in the coil of electrically conductive wire attached to the device. The coil thus detects the change of status of the nuclear spins in the vicinity of the coil. The transmission line transmits the detected response signal to the radio frequency receiver, which processes it and then stores it with the controller. This is repeated in three orthogonal directions. The gradients cause the frequency of the detected signal to be directly proportional to the position of the radio-frequency coil along each applied gradient.

The position of the radio frequency coil inside the patient may therefore be calculated by processing the data using Fourier transformations so that a positional picture of the coil is achieved. In one implementation, this positional picture is superposed with a magnetic resonance image of the region of interest. This picture of the region may be taken and stored at the same time as the positional picture or at any earlier time.

Elongated intravascular devices utilized in association with MRI applications must generally be made from low magnetic susceptible materials, otherwise they will disturb the magnetic resonance (MR) image of the surrounding body tissue. It is not uncommon for elongated intravascular devices, such as catheters and guidewires, to utilize a reinforcement mechanism so as to enable particular desired mechanical characteristics, such as a desired tensile strength or desired features related to flexibility. It is therefore necessary, within the context of MRI-related applications, that reinforcement mechanisms within elongated intravascular devices be made from low magnetic susceptible materials.

Presently, it is not uncommon for an elongated intravascular member, such as a catheter or a guidewire, to incorporate a strand of reinforcement material, or a layer of braided or woven reinforcement material, into a coaxial layer of the elongated member. In non-MRI applications, strands, wires and/or fibers incorporated into these types of reinforcement mechanisms can be constructed of highly magnetic materials such as stainless steel. In many instances, highly magnetic materials demonstrate desirable mechanical characteristics (i.e., a desirable tensile strength, flexibility, etc.) In MRI applications, however, to avoid interference with magnetically generated images, such highly magnetic materials are typically replaced with lower magnetic metals or special alloys (like Tantalum, Elgiloy, MP35N, etc.). In the context of MRI applications, however, all metal materials and metal alloy materials will still have some negative influence on the magnetic image.

In some instances, polymer fibers which have, of course, no negative influence on the magnetic image have been incorporated into elongated intravascular MRI devices for reinforcement. Polymer fibers, however, as compared to the metal and metal alloy materials, have generally inferior mechanical qualities.

The present invention addresses at least one of these and other problems and offers advantages over the prior art.

SUMMARY OF THE INVENTION

The present invention generally pertains to elongated intravascular MRI devices adapted to be advanced through a vessel of a subject. In particular, the present invention provides one or more constructions of such intravascular devices that incorporate reinforcement mechanisms that enable both desirable mechanical qualities and minimal negative magnetic interference with MR imaging.

One embodiment of the present invention pertains to a reinforced magnetic resonance imaging catheter. The catheter comprises an elongated body having at least one lumen extending therethrough. The elongated body also includes a proximal end, a distal end, a circumference, a longitudinal axis running between the proximal and distal ends, and a coaxial layer that incorporates at least one elongated ceramic member. An antenna is operably disposed proximate the distal end of the elongated body.

Another embodiment of the present invention pertains to an elongated medical device for intravascular manipulation during magnetic resonance imaging of body tissue. The device includes an elongated body and a reinforcement mechanism disposed about a portion of the elongated body. The reinforcement mechanism comprises at least one elongated ceramic member.

Another embodiment of the present invention pertains to a reinforcement member for reinforcing an elongated intravascular magnetic resonance imaging device. The reinforcement member comprises an elongated ceramic fiber and a coating disposed about the elongated ceramic fiber.

These and various other features, as well as advantages which characterize the present invention, will be apparent upon a reading of the following detailed description and review of the associated drawings.

BRIEF DESCRIPTION OF THE DRAWINGS

FIG. 1 is a partial block diagram of an illustrative magnetic resonance imaging and intravascular guidance system in which embodiments of the present invention can be employed.

FIG. 2 is a side view of a magnetic resonance catheter in accordance with an illustrative embodiment of the present invention.

FIG. 3 is a cross-sectional view of the catheter shown in FIG. 2.

FIG. 4 is a side view of a portion of a braided or woven coaxial layer according to an illustrative embodiment of the present invention.

FIG. 5 is a side view of a ceramic reinforcement member in accordance with an illustrative embodiment of the present invention.

FIG. 6 is a cross-sectional view of the ceramic reinforcement member of FIG. 5.

FIG. 7 is a partially exposed side view of a guidewire in accordance with an illustrative embodiment of the present invention.

FIG. 8 is a side view of a catheter in accordance with an illustrative embodiment of the present invention.

DETAILED DESCRIPTION OF ILLUSTRATIVE EMBODIMENTS

FIG. 1 is a partial block diagram of an illustrative magnetic resonance imaging and intravascular guidance system in which embodiments of the present invention could be employed. In FIG. 1, subject 100 on support table 110 is placed in a homogeneous magnetic field generated by magnetic field generator 120. Magnetic field generator 120 typically comprises a cylindrical magnet adapted to receive subject 100. Magnetic field gradient generator 130 creates magnetic field gradients of predetermined strength in three mutually orthogonal directions at predetermined times. Magnetic field gradient generator 130 is illustratively comprised of a set of cylindrical coils concentrically positioned within magnetic field generator 120. A region of subject 100 into which a device 150, shown as a catheter, is inserted, is located in the approximate center of the bore of magnetic 120. Illustratively, device 150 could be a guidewire or some other intravascular device.

RF source 140 radiates pulsed radio frequency energy into subject 100 and the MR active sample within device 150 at predetermined times and with sufficient power at a predetermined frequency to nutate nuclear magnetic spins in a fashion well know to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnetic field generator 120 and the local field generated by magnetic field gradient generator 130. In an illustrative embodiment, RF source 140 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils such as surface coils may alternatively be used.

Device 150 is inserted into subject 100 by an operator. Illustratively, device 150 may alternatively be a guidewire, a catheter, an abation device or a similar recanalization device or other intravascular device. Device 150 includes an RF antenna which detects MR signals generated in both the subject and the device 150 itself in response to the radio frequency field created by RF source 140. Since the internal device antenna is small, the region of sensitivity is also small. Consequently, the detected signals have Larmor frequencies which arise only from the strength of the magnetic field in the proximate vicinity of the antenna. The signals detected by the device antenna are sent to imaging and tracking controller unit 170 via conductor 180.

External RF receiver 160 also detects RF signals emitted by the subject in response to the radio frequency field created by RF source 140. In an illustrative embodiment, external RF receiver 160 is a cylindrical external coil that surrounds the region of interest of subject 100. Such an external coil can have a diameter sufficient to have a compass the entire subject 100. Other geometries, such as smaller cylinders specifically designed for imaging the head or an extremity can be used instead. Non-cylindrical external coils, such as surface coils, may alternatively be used. External RF receiver 160 can share some or all of its structure with RF source 140 or can have a structure entirely independent of RF source 140. The region of sensitivity of RF receiver 160 is larger than that of the device antenna and can encompass the entire subject 100 or a specific region of subject 100. However, the resolution which can be obtained from external RF receiver 160 is less than that which can be achieved with the device antenna. The RF signals detected by external RF receiver 160 are sent to imaging and tracking controller unit 170 where they are analyzed together with the RF signals detected by the device antenna.

The position of device 150 is determined in imaging and tracking controller unit 170 and is displayed on display means 190. In an illustrative embodiment of the invention, the position of device 150 is displayed on display means 190 by superposition of a graphic symbol on a conventional MR image obtained by external RF receiver 160. Alternatively, images may be acquired by external RF receiver 160 prior to initiating tracking and a symbol representing the location of the tracked device be superimposed on the previously acquired image. Alternative embodiments of the invention display the position of the device numerically or as a graphic symbol without reference to a diagnostic image.

FIG. 2 is side view of one illustrative embodiment of a device that could be utilized similar to device 150 described above in relation to FIG. 1. More particularly, FIG. 2 is a side view of a magnetic resonance catheter 200 (MR catheter 200), in accordance with an illustrative embodiment of the present invention. MR catheter 200 includes an elongated body 210 having a proximal end 220 and a distal end 230. An antenna 240 may be operably disposed proximate distal end 230 and operates as described above in relation to FIG. 1.

FIG. 3 is a cross-sectional view of MR catheter 200 taken along line 3—3 in FIG. 2. As is illustrated in FIG. 3, MR catheter 200 includes a circumference 310 and an axis 320, that each illustratively extend at least from proximal end 220 to distal end 230. The MR catheter 200 also includes a lumen 330 that also illustratively extends between ends 220 and 230. It should be noted that catheters having additional lumens should be considered within the scope of the present invention.

With further reference to FIG. 3, lumen 330 is illustratively formed and defined by an undercoat layer of a material such as urethane, PVC, polyamide, silicon or some other similar material. Alternatively, a first coaxial layer 340 (i.e., a tightly woven layer 340) may directly define lumen 330. A second coaxial layer 350 is illustratively a protective layer that provides catheter 200 with a substantially smooth outer surface. In accordance with one embodiment, second coaxial layer 350 is constructed of a polymeric material. It should be noted that, without departing from the scope of the present invention, any of the undercoat layer, the first coaxial layer and the second coaxial layers could illustratively be formed of multiple individual layers and/or constructed of any of the above-described or other similar materials.

FIG. 4 is a side view of an exposed portion of first coaxial layer 340, in accordance with an illustrative embodiment of the present invention. First coaxial layer 340, as illustrated, is a braided or woven layer of material that provides reinforcement to catheter 200 (FIG. 2) and enables desirable mechanical characteristics (i.e., desirable tensile strength, flexibility, etc.) that are particularly useful in the context of intravascular manipulation of catheter 200 (FIG. 2) during magnetic resonance imaging.

With further reference to FIG. 4, layer 340 includes sectional bundles 410 of individual reinforcement members 420. Illustratively, reinforcement members 420 may be wires, fibers or some other elongated element that can be bent and braided or woven as illustrated. It is to be emphasized that the particular braid/weave pattern illustrated in FIG. 4 is illustrative only. Reinforcement members 420 could be alternatively braided or woven in an almost limitless range of other patterns without departing from the scope of the present invention. Such patterns may or may not include sectional bundles 410.

FIG. 5 is a side view of one illustrative embodiment of a reinforcement member that could be utilized similarly to any of reinforcement members 420 described above in relation to FIG. 4. More particularly, FIG. 5 is a side view of a ceramic reinforcement member 500, in accordance with an illustrative embodiment of the present invention. Ceramic reinforcement member 500 is constructed of low or non-magnetic materials and therefore will not disturb an MR image of body tissue that surrounds an associated MRI device.

Ceramic reinforcement member 500 is a coated ceramic member, illustratively a coated ceramic fiber. FIG. 6 is a cross-sectional view of member 500 taken along line 6—6 in FIG. 5 and shows that member 500 includes a ceramic core 610 and a coating 620. In accordance with an embodiment of the present invention, the mechanical characteristics and mechanical quality of ceramic reinforcement member 500 are comparable to a highly magnetic metal member, such as a stainless steel member.

Coating 620 is disposed on ceramic core 610 and illustratively makes it possible for member 500 to be bent without breaking, thereby enabling member 500 to be woven similar to reinforcement members 420 in FIG. 4 (but not necessarily in the same FIG. 4 configuration). Ceramic materials often have normally low bending resistance due, at least in part, to surface scratches that are inherent to the material. In some instances, surface scratches are intentionally applied to create or enhance certain mechanical characteristics. Regardless of the source of the scratches, coating 620 fills the scratches and allows the fibers to be bent and to be incorporated into a braiding or weaving process. Notably, a ceramic reinforcement member, such as member 500, can be processed up to a very high temperature, which allows it to go through an extrusion process. Ceramic reinforcement member 500 is additionally advantageous in that it can be incorporated into a woven layer using operations identical to known operations used to braid wires or fibers constructed of high magnetic material, such as metal wires, strands, fibers, etc. Ceramic reinforcement member 500 includes mechanical properties similar to metal or metal alloy fibers but does not include an associated disadvantageous potential for magnetic disturbance of magnetic resonance imaging.

In accordance with illustrative embodiments of the present invention, ceramic core 610 is constructed of a material that includes carbon (C), silicon carbide (SiC) and/or aluminum oxide ($Al_2O_3$). Illustratively, coating 620 may comprise a polymeric material or a material that includes pyrolytic carbon (PyC). All of these materials should be considered illustrative examples only. Other similar materials could be utilized without departing from the scope of the present invention.

It should be pointed out that FIG. 4 is only one illustrative example of how ceramic reinforcement member 500 (FIG. 5) might be utilized as at least one of the reinforcement members 420. It should be noted that not all members 420 need be constructed similar to ceramic reinforcement member 500. For example, in accordance with one embodiment, some of the individual reinforcement members could be constructed similar to FIG. 5 while others are otherwise constructed. For example, some of the members 420 could be constructed of polymeric or other low or non-metallic materials. It is conceivable that an elongated intravascular member, such as catheter 200 (FIG. 2) could achieve desirable mechanical qualities utilizing a braided or woven reinforcement layer that combines multiple members similar to ceramic reinforcement member 500 with other low or non-metallic reinforcement members.

It should be noted that the ceramic reinforcement members of the present invention could be incorporated into MRI-related elongated intravascular devices other than MR catheters. For example, FIG. 7 is a partially exposed side view of a guidewire 700 in accordance with an illustrative embodiment of the present invention. Guidewire 700 may (or may not) illustratively include an MRI-related antennae similar to antennae 240 described in relation to FIG. 2. Guidewire 700 includes a coating 705 that has been partially exposed at sections 710 for the purpose of illustration. Exposed portions 710 reveal that coating 705 covers a braided or woven portion 720. Illustratively, braided or woven portion 720 may or may not cover the entire length of guidewire 700. In accordance with an embodiment of the present invention, braided or woven portion 720 includes one or more reinforcement members similar to member 500 described above in relation to FIGS. 5 and 6. Braided or woven portion 720 illustratively axially engages a central wire portion 730. FIG. 7 is only intended to illustrate that the present invention could be applied in contexts other than that of an MR catheter. Precise configurations and braid or weave patterns may vary without departing from the scope of the present invention. The present invention could apply still to MRI-related elongated intravascular devices other than MR catheters and MR guidewires.

FIG. 8 is a side view of a catheter 800 in accordance with an illustrative embodiment of the present invention. Catheter 800 includes a lumen 830 that is similar to lumen 330 described above in relation to FIG. 3 and a layer 840 that is similar to layer 350 also described in relation to FIG. 3. A ceramic reinforcement member 820 is sandwiched between lumen 830 and layer 840. Member 820 is a single non-braided or woven member and is constructed of a covered ceramic member similar to member 500 described above in relation to FIGS. 5 and 6. Points 805 and 815 have been labeled to visibly clarify the circumferentially-wrapped nature of the reinforcement member. Illustratively, additional members 820 could be incorporated between lumen 830 and layer 840 of catheter 800. Catheter 800 is intended to illustrate that, in accordance with embodiments of the present invention, ceramic reinforcement members need not always be applied in a braided or woven configuration.

Although the present invention has been described with reference to illustrative embodiments, workers skilled in the art will recognize that changes may be made in form and detail without departing from the spirit and scope of the invention.

What is claimed is:

1. A reinforced magnetic resonance imaging catheter, comprising:
    an elongated body having at least one lumen extending therethrough, the elongated body further comprising a proximal end, a distal end, a circumference, a longitudinal axis running between said proximal and distal ends, and a coaxial layer that incorporates at least one elongated ceramic member; and
    an antenna operably disposed proximate the distal end of the elongated body.

2. The reinforced magnetic resonance imaging catheter of claim 1 wherein the elongated ceramic member is substantially covered with a coating.

3. The reinforced magnetic resonance imaging catheter of claim 2, wherein the elongated ceramic member comprises applied surface scratches, and the coating substantially fills the applied surface scratches, enabling an enhanced flexibility wherein the ceramic fiber can be bent without breaking.

4. The reinforced magnetic resonance imaging catheter of claim 2, wherein the coating includes a pyrolytic carbon material.

5. The reinforced magnetic resonance imaging catheter of claim 1, wherein the elongated ceramic member is of an overall flexibility that it can be bent without breaking.

6. The reinforced magnetic resonance imaging catheter of claim 1, wherein the coaxial layer is a woven layer of fibers that reinforce the elongated body and the elongated ceramic member is a ceramic fiber woven together with non-ceramic fibers into the woven layer.

7. The reinforced magnetic resonance imaging catheter of claim 1, wherein the elongated ceramic member is wrapped around the elongated body.

8. The reinforced magnetic resonance imaging catheter of claim 1, wherein the elongated ceramic member includes a silicon carbide material.

9. The reinforced magnetic resonance imaging catheter of claim 1, wherein the elongated ceramic member includes a carbon material.

10. The reinforced magnetic resonance imaging catheter of claim 1, wherein the elongated ceramic member includes an aluminum oxide material.

11. An elongated medical device for intravascular manipulation during magnetic resonance imaging of body tissue, comprising:
    an elongated body;
    an antenna operably disposed proximate the distal end of the elongated body; and
    a reinforcement mechanism disposed about a portion of said elongated body, the reinforcement mechanism comprising at least one elongated ceramic member.

12. The elongated medical device of claim 11, wherein the elongated ceramic member is substantially covered with a coating.

13. The elongated medical device of claim 12, wherein the coating is a polymeric coating.

14. The elongated medical device of claim 12, wherein the coating includes a pyrolytic carbon material.

15. The elongated medical device of claim 11, wherein the elongated ceramic member is of an overall flexibility that it can be bent without breaking.

16. The elongated medical device of claim 11, wherein the reinforcement mechanism is a woven layer of fibers that reinforce the elongated body and the elongated ceramic member is a ceramic fiber woven together with non-ceramic fibers into the woven layer.

17. The elongated medical device of claim 11, wherein the elongated ceramic member is wrapped around the elongated body.

18. The elongated medical device of claim 11, wherein the elongated ceramic member includes a silicon carbide material.

19. The elongated medical device of claim 11, wherein the elongated ceramic member includes a carbon material.

20. The elongated medical device of claim 11, wherein the elongated ceramic member includes an aluminum oxide material.

21. A reinforcement member for reinforcing an elongated intravascular magnetic resonance imaging device, the reinforcement member comprising:
    an elongated ceramic fiber comprising applied surface scratches; and
    a coating disposed about the elongated ceramic fiber, substantially filling the applied surface scratches, enabling an enhanced flexibility wherein the ceramic fiber can be bent without breaking.

22. The reinforcement member of claim 21, wherein the coating is a polymeric coating.

23. The reinforcement member of claim 21, wherein the coating includes a pyrolytic carbon material.

24. The reinforcement member of claim 21, wherein the elongated ceramic fiber is of an overall flexibility that it can be bent without breaking.

25. The reinforcement member of claim 21, wherein the elongated ceramic fiber includes a silicon carbide material.

26. The reinforcement member of claim 21, wherein the elongated ceramic fiber includes a carbon material.

27. The reinforcement member of claim 21, wherein the elongated ceramic fiber includes a aluminum oxide material.

* * * * *